United States Patent [19]

Thone

[11] Patent Number: 4,704,898

[45] Date of Patent: Nov. 10, 1987

[54] METHOD AND APPARATUS FOR MEASURING THE VISCOSITY OF A LIQUID

[76] Inventor: Ernst Thone, Sorenkoppel 10 e, 2000 Hamburg 73, Fed. Rep. of Germany

[21] Appl. No.: 768,011

[22] Filed: Aug. 21, 1985

[51] Int. Cl.[4] ............................................. G01N 11/16
[52] U.S. Cl. ....................................................... 73/54
[58] Field of Search ...................................... 73/54, 59

[56] References Cited

U.S. PATENT DOCUMENTS

| | | | |
|---|---|---|---|
| 2,839,915 | 6/1958 | Roth et al. | 73/59 |
| 3,286,507 | 11/1966 | Moore | 73/54 X |
| 3,474,663 | 10/1969 | Whitmer et al. | 73/54 |
| 3,525,252 | 8/1970 | Kocatas | 73/54 |
| 3,587,295 | 6/1971 | Simons | 73/54 X |
| 4,558,588 | 12/1985 | Beaudoin et al. | 73/54 |

FOREIGN PATENT DOCUMENTS

| | | | |
|---|---|---|---|
| 15837 | 1/1984 | Japan | 73/54 |
| 685958 | 9/1979 | U.S.S.R. | 73/54 |
| 890150 | 12/1981 | U.S.S.R. | 73/54 |

*Primary Examiner*—Stewart J. Levy
*Assistant Examiner*—Joseph W. Roskos
*Attorney, Agent, or Firm*—Fliesler, Dubb, Meyer & Lovejoy

[57] ABSTRACT

Method and apparatus for measuring the viscosity of a liquid is set forth wherein an oscillating element is used to cause excitation of a comparative medium and the damping behavior of the comparative medium is determined as a function of time. The same oscillating element is used to determine the damping behavior of the test liquid as a function of time. The thus measured damping behaviors are compared to determine the viscosity of the liquid.

6 Claims, 2 Drawing Figures

METHOD AND APPARATUS FOR MEASURING THE VISCOSITY OF A LIQUID

The invention relates to a method for measuring the viscosity of a liquid by an excitation causing an oscillation of the liquid, the vibrational behavior of which in a comparative medium of known viscosity is known, and the modification of which under the influence of the liquid is determined.

The invention further relates to an apparatus for measuring the viscosity of a liquid, which is constructed as an oscillator which excites the liquid, the oscillations of which executed in a comparative medium are known, and which exhibits an indicator showing the differences in the vibrational behavior.

Various methods of measurement, based on different principles, are known for measuring viscosity. In the capillary viscosimeter the knowledge is utilized that the dynamic viscosity is proportional either to a measured $\Delta p$ or to the required energy which is necessary to obtain this pressure difference. However, this assumption is valid with sufficient accuracy only in the range of small flow velocities. Furthermore, only small measurement ranges are covered by this means. Moreover, in a number of cases of practical importance, for example in the measurement of oil viscosities for example, the fact that the limiting conditions must be maintained as constant as possible for this method of measurement acquires considerable importance. In order to obtain sufficient accuracy of measurement, both the volume flows and the physical dimensions of the capillaries must therefore be kept as constant as possible. In the determination of the viscosity of oil in particular, these limiting conditions can be fulfilled only by a great outlay, because the volume flows vary according to the requirements of, for example, an internal-combustion engine, and the capillaries easily become fouled, particularly in the case of pool qualities of oil.

In addition, rotary viscosimeters are known, which require high precision production in view of the substantial dynamic loading. This results in a considerable technical outlay, which is reflected in a corresponding production price. Such rotary viscosimeters are therefore only economically justifiable under particularly favorable conditions of production and installation.

Lastly, damping viscosimeters are known, in which the damping of a given oscillation is measured. The measurement of the damping presented considerable difficulties hitherto, so that the damping viscosimeter has not played an important part in practical metrology. In particular, it was impossible to prevent the measurement result from being influenced by the vibrational behavior of an apparatus by which the liquid was required to be set in oscillation. This vibrational behavior is a function of the degree of fouling of the apparatus. With increasing fouling of the apparatus, it was impossible to determine to what extent the measurement result had been influenced by the fouling.

It is therefore the aim of the present invention improve the method of the type initially stated so that it yields a verifiable measurement result which corresponds to the true viscosity of the liquid.

This aim is achieved according to the invention in that, in order to determine the modification of the oscillation, the energies absorbed in order to generate it in the comparative medium on the one hand and in the liquid on the other hand are measured and the difference of the measured energies is then determined as a measure of the damping which occurs in the liquid.

The energies required to generate the various oscillations can be measured accurately without problems by a relatively small measurement outlay. Furthermore, during the energy measurement, measured value jumps appear which indicate an increasing fouling of the apparatus by means of which the oscillations are generated. In this way measurable guidance is obtained that, due to the fouling which has occurred, the apparatus may no longer yield measured values corresponding to the true viscosity. Appropriate countermeasures can be adopted. Furthermore, the apparatus can easily be adjusted, by modest means, relative to the known viscosity of a comparative medium. For example, it is conceivable to adjust the apparatus relative to air. Then, for this purpose, the apparatus is withdrawn from the liquid to be measured and adjusted relative to the ambient air. Finally it is conceivable to introduce the measured value obtained by this means, without difficulty, into an open loop and closed loop control system. By means of such a system it is possible to ensure that the viscosity of the liquid is adapted to given conditions, for example the fuel for internal-combustion engines is supplied to the latter with constant viscosity.

The apparatuses hitherto known for measuring viscosity either yielded inaccurate measurement results or were expensive both to produce and to operate, because highly qualified measuring staff had to be employed for their use.

It is therefore a further aim of the present invention to improve the apparatus of the type initially stated so that it is simple and cheap to produce and yields practically useful measurement result with sufficient accuracy even to inexperienced measurement personnel.

This aim is achieved according to the invention in that the oscillator is constructed as a paddle provided with an oscillation exciter.

The paddle excited by means of the oscillation exciter undergoes a damping in the liquid, the viscosity of which is required to be determined. This damping is measured in a simple manner already described, by way of a comparison of the energy absorbed. Furthermore, the vibrational behavior of the paddle in a comparative medium, for example air, is known. The paddle can easily be adjusted relative to the comparative medium. It is furthermore made possible in a manner which permits simple maintenance. It is protected from inadmissible fouling by the smoothest possible surfaces. If fouling of the paddle should nevertheless occur, this can be detected very easily in that the vibrational behavior of the paddle changes abruptly. This results in measured value jumps, which provide good indications of the fouling of the paddle which has occurred. Finally, it is conceivable to clean the paddle by simple means, so that it reassumes its original vibrational behavior, to which the measurement results recorded can be referred.

Further particulars of the invention will emerge from the following thorough description and from the accompanying drawings, in which a preferred exemplary embodiment of the invention is illustrated by way of example.

Figure 1:
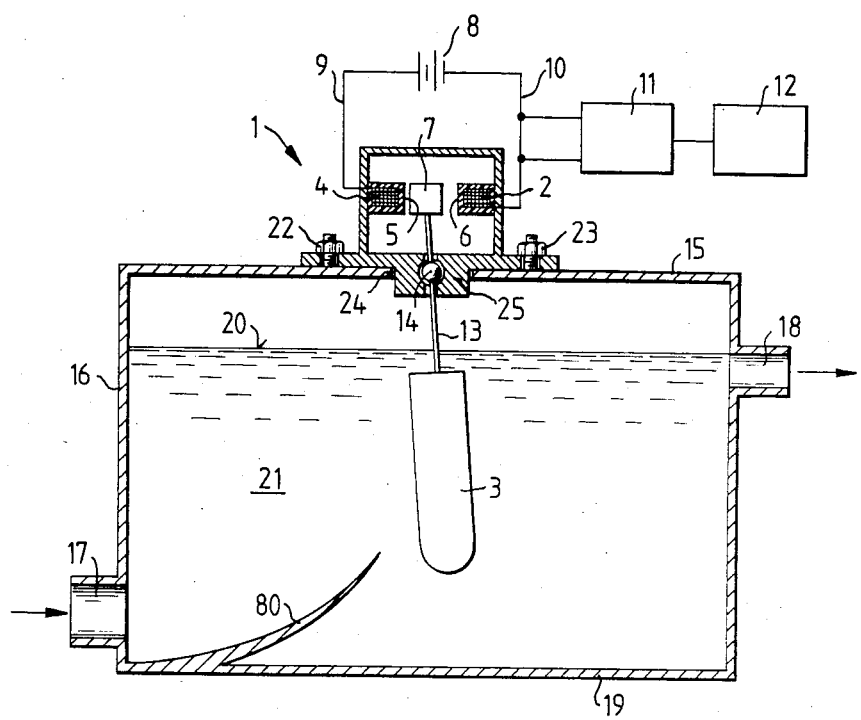
FIG. 1 shows a diagrammatic view of an apparatus for measuring viscosity.
Figure 2:
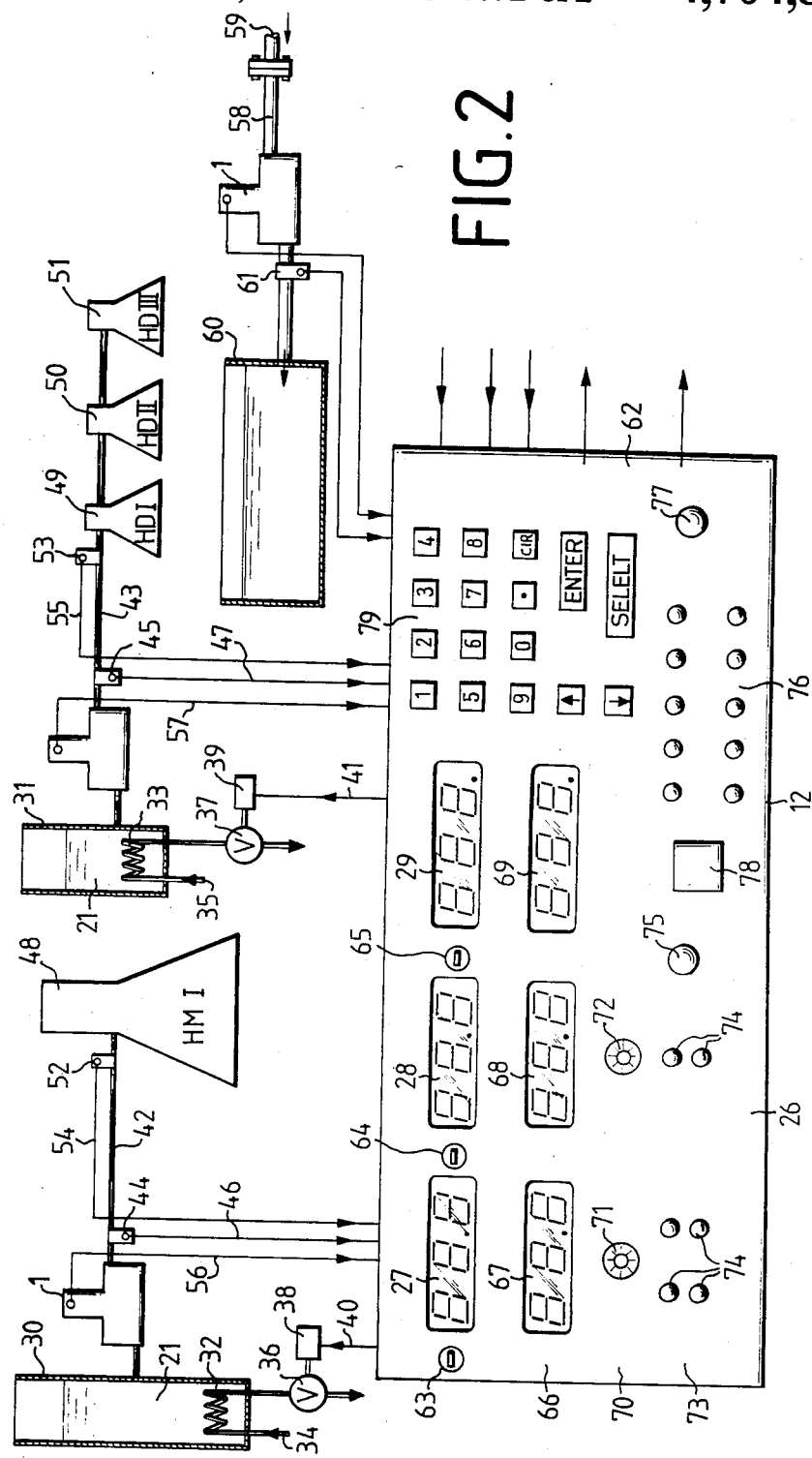
FIG. 2 shows a diagrammatic view of a closed loop control installation for maintaining the viscosity constant.

The method according to the invention is conveniently performed with an apparatus 1, which is illustrated by way of example in FIG. 1. It consists substantially of an oscillation exciter 2 and of a paddle 3. The oscillation exciter may be constructed as an electromagnet 4, between the two poles 5, 6 of which an iron core 7 is mounted. The two poles 5, 6 are connected to an alternating voltage which corresponds to that of an electricity souce 8. The supply of the poles 5, 6 occurs via leads 9, 10, which are connected via a meter 11 to a computer 12. The meter 11 may, for example, determine the modification of the energy absorption of the electromagent 4. It may be constructed as an ammeter or voltmeter, for example. The iron core 7 is connected via a coupling 13 to the paddle 3. This coupling 13 may be constructed as a fixed connecting rod which is mounted in a swivel bearing 14. This swivel bearing 14 is attached in the region of a cover 15, through which the coupling 13 projects into a tank 16 which is covered by the cover 15. This tank 16 contains a liquid 21, into which the paddle 3 dips for the purpose of measuring its viscosity. The tank 16 is provided with an inlet 17 and an outlet 18. The inlet 17 may be adjacent to a base plate 19 placed opposite the cover 15, which forms the bottom boundary of the tank 16. On the other hand, the outlet 18 determines a level 20 corresponding to a liquid level provided in the tank 16. This outlet 18 will therefore generally be placed facing the cover 15. It is however also conceivable to construct the tank 16 in a different manner, if it is thereby ensured that the paddle 3 dips sufficiently deeply into the liquid 21.

The oscillation exciter 2 is arranged in such a way relative to the inlet 17 or outlet 18 that the paddle 3 can execute oscillations, the direction of which extends transversely to the flow direction of the liquid 21 flowing through the tank 16. It is however also conceivable that the paddle 3 executes oscillations which are oriented parallel to the flow direction.

The paddle 3 is first of all adjusted in a comparative medium. This comparative medium may be, for example, ambient air present in the region of the tank 16. The oscillation exciter 2 is then attached to the cover 15 of the tank 16 by means of screw connections 22, 23. The paddle 3 is then introduced through an orifice 24 which is present at an appropriate point in the cover 15. The orifice 24 is provided with a closure 25 sealing the cover 15.

After the tank 16 has been filled with liquid 21, the oscillation exciter 2 is connected to the voltage of the electricity source 8, so that the iron core 7 is set in oscillation. The paddle 3 oscillates in corresponding manner. The oscillation exciter 2 then absorbs an energy which differs from that which the oscillation exciter absorbed when it was adjusted in the ambient air. Both the energy absorbed during adjustment, and also that which is necessary to set the paddle 3 in oscillation in the liquid 21, is measured by the meter 11. The two measured values are fed into the computer 12, which compares the two quantities of energy. It determines an energy difference, the value of which corresponds to the viscosity of the liquid 21. The computer 12 can convert the calculated energy difference so that a data output 26 provided on the computer 12 indicates the viscosity of the liquid 21 directly. Corresponding indicators 27, 28, 29 are provided for this purpose. Because the viscosity of a liquid 21 is a function of its temperature, the measurement result obtained is also a function of the temperature. In order to obtain comparable measurement results, a heat transfer device 30, 31 is provided, in which the liquid 21 is maintained at a given temperature by a heating apparatus 32, 33. This heating apparatus 32, 33 may be constructed as a steam heater, the temperature delivered by which is a function of the inflow of a given quantity of steam 34, 35, the quantity of which flowing into the heating apparatus 32, 33 is controlled by a control valve 36, 37. This control valve 36, 37 is provided with an adjustable drive 38, 39, which is connecteo via a control line 40, 41 to the computer 12.

In addition, an apparatus 44, 45 is provided in a fuel pipe 42, 43 adjacent to the outlet 18 for measuring the temperature of a liquid leaving the apparatus 1 in immediate proximity of the apparatus 1. These apparatuses 44, 45 are also connected via corresponding control lines 46, 47 to the computer 12.

The fuel pipes 42, 43 may lead to internal-combustion engines 48, 49, 50, 51 which are supplied with fuel through the fuel pipes 42, 43. The internal-combustion engines 48, 49, 50, 51 may, for example, be such as are installed on board ships. The internal-combustion engine 48 represents the main engine, and the internal-combustion engines 49, 50, 51 represent the ship's auxiliary diesels.

A further devlce 52, 53 for measurlng the temperature of the fuel entering the internal-combustion engines 48, 49, 50, 51 is provided immediately before the entry of the fuel pipes 42, 43 into the internal-combustion engines 48, 49, 50, 51. These devices 52, 53 are connected via control lines 54, 55 to the computer 12.

As a rule, there exists between the apparatus 1 and the internal-combustion engines 48, 49, 50, 51 a relatively great interval, across which heat losses of the liquid flowing through the fuel pipes 42, 43 may occur. As a result of these heat losses, the liquid 21 arrives in the internal-combustion engines 48, 49, 50, 51 with a different viscosity than that measured in the apparatus 1. The viscosity change which then occurs corresponds substantially to the heat loss occurring in the fuel pipe 42, 43. The temperature variation resulting from this is measured by the devices 52, 53 and acquired by the computer 12. Depending upon the value of the heat loss, the viscosity of the liquid 21 must be corrected by raising the temperature in the region of the heat transfer device 30, 31, by means of the computer 12, the quantity of steam flowing through the heating device 32, 33 is controlled so that the apparatus 1 measures a viscosity of the liquid 21 which, taking into consideration the heat loss in the fuel pipe 42, 43, has on enetering the internal-combustion engines 48, 49, 50, 51 a constant value which is dictated by the requirement of the internal-combustion engines 48, 49, 50, 51.

As a measure of the viscosity existing upon entry into the internal-combustion engine 48, 49, 50, 51, the devices 52, 53 measure the temperature of the liquid 21 entering the internal-combustion engine 48, 49, 50, 51. Having regard to the viscosity, measured by the apparatus 1, of the liquid 21 flowing through the fuel pipes 42, 43, the heat surrendered by the heating device 32, 33 is controlled by the computer 12 so that the viscosity of the liquid 21 which is demanded by the internal-combustion engine 48, 49, 50, 51 exists upon entry into the internal-combustion engine 48, 49, 50, 51.

If the apparatus 1 detects that the viscosity of the liquid 21 varies at constant temperature, then it delivers a corresponding control signal via corresponding control lines 56, 57 to the computer 12. The computer 12 converts the viscosity variation reported by the apparatus 1 into a temperature variation which is necessary in order to have a constant viscosity in the liquid 21 in front of the internal-combustion engine 48, 49, 50, 51. The supply of steam to the heating device 32, 33 is adapted via the adjustable drive 38, 39 in corresponding manner. The effect of this variation as regards the temperature of the liquid 21 on entry into the internal-combustion engine 48, 49, 50, 51 is measured by the devices 52, 53. If these devices 52, 53 detect that the liquid 21 upon entry into the internal-combustion engine 48, 49, 50, 51 is not at the temperature determined by the computer 12, which corresponds to the viscosity demanded upon entry into the internal-combustion engine 48, 49, 50, 51, then the computer 12 performs a correction of the steam supply by actuating the adjustable drive 38, 39 until, in conformity with the viscosity of the liquid 21 determined by the apparatus 1, the temperature of the liquid 21 determined by the computer 12 prevails at the entry into the internal-combustion engine 48, 49, 50, 51.

The control of the viscosity of the liquid 21 which operates in this manner may also be utilized in order to monitor the viscosity of a liquid 21 which is required to be delivered to a customer with given quality features. It is conceivable, for example, to monitor the quality of a fuel which is being pumped on board a ship.

This fuel is pumped through a bunker pipe 58 and a supply station located on shore and not shown, which is connected to the bunker pipe 57 by a supply pipe 59, into a bunker 60 located on board the ship. An apparatus 1, which is arranged within the bunker pipe 58, measures the viscosity of the fuel flowing through the bunker pipe 58. A device 61 for measuring the temperature of the fuel flowing through the bunker pipe 58 is provided in immediate proximity, for example immediately behind the apparatus 1 in the direction of flow of the fuel. Both the apparatus 1 for measuring the viscosity and also the apparatus 61 for measuring the temperature are connected to the computer 12. By virtue of the program input into the computer 12, the latter is able to convert the viscosity of the fuel flowing through the bunker pipe 58, measured by the apparatus 1, to a different viscosity which the fuel flowing through the bunker pipe 58 ought to exhibit at a different temperature, for example at a standard temperature, or at a temperature agreed with a supplier of the fuel. The computer indicates the viscosity calculated in this manner in its indicator 29. If this indicator 29 deviates from the viscosity of the bunkered fuel agreed with the supplier, then measures can be adopted, for example, in the case of poor quality of the bunkered fuel, the price may be reduced or the bunkered fuel may be returned.

Finally it is conceivable for the computer 12 to be used for monitoring purposes with the assistance of the indicators 27, 28, 29. The indicators 27, 28, 29 may be stored on a data carrier, for example. In this manner the qualities of the fuel with which the internal-combustion engines 48, 49, 50, 51 have been supplied can be recalled from the data carrier in case of need. The recalled data gives information on the time at which all or individual internal-combustion engines 48, 49, 50, 51 have been supplied with what quality of fuel.

The operation of the computer 12 is facilitated by the data output 26. The data output 26 is integrated in a display panel 62 which may be provided, for example, in the region of a control position which is used to operate the internal-combustion engines 48, 49, 50, 51. On this display panel 62 the indicators 27, 28, 29 for the viscosity are contained in an upper row 63. The indicator 27 serves to indicate the measurement result of the apparatus 1 which measures the viscosity of the fuel supplied to the main engine 48. The indicator 28 reproduces the measurement result of apparatus 1 which measures the viscosity of the fuel supplied to the auxiliary diesels 49, 50, 51. The indicator 29 indicates, converted to a reference temperature, for example 50° C., the result of the apparatus 1 which measures the viscosity of the fuel flowing through the bunker pipe 58.

The indicators 27, 28 may furthermore be associated with selector switches 64, 65, upon the actuation of which the indicator 27 or 28 indicates either the DESIRED value of the viscosity which the fuel supplied to the respective internal-combustion engines 48, 49, 50, 51 is required to possess, or the ACTUAL value which has been measured respectively by the apparatuses 1.

In a row 66 which extends below the row 63, indicators 67, 68, 69 are arranged which reproduce the measurement result of apparatuses 44, 45, 61 or devices 52, 53. These measurement results include temperature statements, which permit a precise monitoring of the temperature conditions in the fuel pipes 42, 43 and in the bunker pipe 48.

Selector switches 71, 72 are arranged in a further row 70 which is provided below the row 66. By means of these selector switches 71, 72 the indicators 27, 28, 29 and 67, 68, 69 can be made accessible to various measured values and/or computed values. For example, the selector switches 71, 72 can be adjusted to a temperature 1. In this position the indicators 67, 68 indicate the temperatures in the region of the apparatuses 1 determined by the apparatuses 44, 45. In the position temperature II the temperatures measured by the devices 52, 53 are obtained. In the position Visco, the viscosities of the fuel determined by the apparatuses 1 are indicated in the indicators 27, 28. In the position Visco at 50° C., the indicators 27, 28 indicate computed results of the computer 12, which has converted the viscosity determined by the apparatus 1 to a reference temperature of 50° C.

A further row 73 is provided below the row 67. In this row 73 filament lamps 74 are associated mutually in pairs. In each case one pair of filament lamps 74 is associated with the internal-combustion engine 48 or with another main engine, now shown, whereas only one pair of filament lamps 74 is provided for the other internal-combustion engines 49, 50, 51. These filament lamps 74 indicate whether or not the heating devices 32, 33 are being supplied with steam for the purpose of heating the liquid 21. If the computer 12 has determined too low a temperature, then the control valves 36, 37 are opened by the adjustable drives 38, 39. In this case the respective upper filament lamp 74 of the arranged pairs lights up. As soon as the computer 12 has computed a sufficient heating of the liquid 21, the control valves 36, 37 are closed. In this case the lower filament lamps 74 light up.

A field with alarm devices may further be provided in the row 73. This field is sub-divided into an indicator for collective alarm 75, an indicator for detail alarm 76, and an indicator for a cleaning recommendation 77. All the indicators 75, 76, 77 are constructed as filament lamps, but may simultaneously also be connected to an acoustic alarm device. The indicators for the detail alarm 76 light up when temperatures pass above or below specific values, both in the region of the fuel pipe 42 for supplying the internal-combustion engine 48, and also in the region of the fuel pipe 43 for supplying the internal-combustion engines 49, 50, 51 and lastly also in the region of the bunker pipe 68. Furthermore, the indicators 76 also indicate when the viscosity measured by the meters 1 in the various pipes 42, 43, 58 passes above or below a specific value. Independently of the indicator for the detail alarm 76, the indicator for the collective alarm 75 lights up when the computations made by the computer 12 show that the internal-combustion engines 48, 49, 50, 51 or the bunker 60 are not being supplied with the correct fuel. Finally, the indicator 77 for the cleaning recommendation lights up if it should prove, by measured value jumps, that the apparatuses 1 are yielding measured value results which are influenced by a further fouling of the apparatuses 1.

All these indicators 75, 76, 77 light up until they have been extinguished by a cancelling switch 78. The latter may only be actuated when the reason for the alarm indications has been eliminated and the installation has thereby been placed in a prescribed operational state.

Finally, an input field 79, which is provided on display panel 62, serves substantially for programing the computer 12. This input field 79 is provided with digital selector switches and actuating switches by means of which a selection for the input and output of the chosen digits can be made.

Independently of the application example selected, the apparatus 1 may also be used for measuring viscosity in other cases where it is required to determine the viscosity of a liquid. On the other hand, however, the closed loop and open loop control system illustrated may also be equipped with different transducers for measuring the viscosity.

I claim:

1. Apparatus for measuring the viscosity of a liquid comprising an oscillator for exciting the liquid to perform a multiplicity of oscillations, the damping of which executed in a comparative medium with the same oscillator is known, and wherein the oscillator is constructed as a paddle connected to an oscillation exciter; means for comparing the difference in the damping behavior of the oscillations appearing in the liquid with the damping behavior of the oscillation using the same oscillator in the comparative medium by determining the time required for a given damping of the oscillations of the oscillation exciter in the liquid; and means for computing the viscosity of the liquid from the time thus determined, in combination with an internal combustion engine into which fuel is injected and further including a fuel preheater which controls the temperature of the fuel; a temperature measuring element arranged immediately upstream of the internal combustion engine; said apparatus serving as a viscosity meter and being located at an interval from the internal combustion engine, and wherein the computer includes a closed control loop which controls the viscosity immediately upstream of the internal combustion engine as a function of the temperature as measured immediately upstream of the internal combustion engine and as a function of the viscosity determined by the viscosity meter.

2. Apparatus for measuring the viscosity of a liquid, comprising an oscillator for exciting the liquid to perform a multiplicity of oscillations, the damping of which executed in a comparative medium with the same oscillator is known, and wherein the oscillator is constructed as a paddle connected to an oscillator exciter; means for comparing the difference in the damping of the amplitude during a given time of oscillation in the liquid with the damping of the amplitude during a given time of oscillations using the same oscillator in the comparative medium; and means for computing the viscosity of the liquid from the thus determined damping of the amplitude, in combination with an internal combustion engine into which fuel is injected and further including a fuel preheater which controls the temperature of the fuel; a temperature measuring element arranged immediately upstream of the internal combustion engine; said apparatus serving as a viscosity meter and being located at an interval from the internal combustion engine, and wherein the computer includes a closed control loop which controls the viscosity immediately upstream of the internal combustion engine as a function of the temperature as measured immediately upstream of the internal combustion engine and as a function of the viscosity determined by the viscosity meter.

3. In a method of measuring viscosity of a liquid using an oscillating element to cause excitation of the liquid, the improvement comprising;
    measuring the damping behavior of a comparative medium of known viscosity as a function of time using said oscillating element; and
    comparing the thus measured damping behaviors and thereby determining the viscosity of the liquid;
    wherein a measured value determined for the viscosity is introduced into a closed loop control system which maintains the viscosity of the liquid constant;
    wherein the temperature of the liquid is controlled to maintain the viscosity of the liquid;
    wherein the method includes measuring the temperature of the fuel immediately upstream of the internal-combustion engine and its viscosity at an interval from the internal-combustion engine and heating the fuel according to the temperature of the fuel immediately upstream of the engine in the sense that the viscosity of the liquid immediately upstream of the engine is controlled to a given viscosity taking into consideration the distance between the viscosity measuring and the temperature measuring.

4. Apparatus for measuring the viscosity of a liquid comprising an oscillator for exciting the liquid to perform a multiplicity of oscillations, the damping of which executed in a comparative medium with the same oscillator is known, and wherein the oscillator is constructed as a paddle connected to an oscillation exciter; means for comparing the difference in the damping behavior of the oscillations appearing in the liquid with the damping behavior of the oscillation using the same oscillator in the comparative medium by determining the time required for a given damping of the oscillations of the oscillation exciter in the liquid; and means for computing the viscosity of the liquid from the time thus determined, in combination with an energy generator which consumes fuel and into which the fuel is introduced and further including a fuel preheater which controls the temperature of the fuel; a temperature measuring element arranged immediately upstream of the energy generator; said apparatus serving as a viscosity meter and being located at an interval from the energy generator, and wherein the computer includes a closed control loop which controls the viscosity immediately upstream of the energy generator as a function of the temperature as measured immediately upstream of the energy generator and as a function of the viscosity determined by the viscosity meter.

5. Apparatus for measuring the viscosity of a liquid, comprising an oscillator for exciting the liquid to perform a multiplicity of oscillations, the damping of which executed in a comparative medium with the same oscillator is known, and wherein the oscillator is constructed as a paddle connected to an oscillator exciter; means for comparing the difference in the damping of the amplitude during a given time of oscillation in the liquid with the damping of the amplitude during a given time of oscillations using the same oscillator in the comparative medium; and means for computing the viscosity of the liquid from the thus determined damping of the amplitude, in combination with an energy generator which consumes fuel and into which the fuel is introduced and further including a fuel preheater which controls the temperature of the fuel; a temperature measuring element arranged immediately upstream of the energy generator; said apparatus serving as a viscosity meter and being located at an interval from the energy generator, and wherein the computer includes a closed control loop which controls the viscosity immediately upstream of the energy generator as a function of the temperature as measured immediately upstream of the energy generator and as a function of the viscosity determined by the viscosity meter.

6. In a method of measuring viscosity of a liquid using an oscillating element to cause excitation of the liquid, the improvement comprising:

measuring the damping behavior of the liquid using said oscillating element as a function of time;

measuring the damping behavior of a comparative medium of known viscosity as a function of time using said oscillating element; and comparing the thus measured damping behaviors and thereby determining the viscosity of the liquid;

wherein a measured value determined for the viscosity is introduced into a closed loop control system which maintains the viscosity of the liquid constant;

wherein the temperature of the liquid is controlled to maintain the viscosity of the liquid;

wherein the liquid is a fuel adapted to power an energy generator, the fuel is injected into the energy generator; and wherein the method includes measuring the temperature of the fuel immediately upstream of the energy generator and its viscosity at an interval from the energy generator and heating the fuel according to the temperature of the fuel immediately upstream of the energy generator in the sense that the viscosity of the liquid immediately upstream of the energy generator is controlled to a given viscosity taking into consideration the distance between the viscosity measuring and the temperature measuring.

* * * * *